United States Patent [19]

Shimano et al.

[11] Patent Number: 4,627,981
[45] Date of Patent: Dec. 9, 1986

[54] **ATTRACTANT-INGESTION STIMULANT PREPARATIONS FOR *PERIPLANETA AMERICANA* L**

[75] Inventors: Kimihide Shimano, Shiraoka; Haruo Shimamura, Yono; Hiroshi Yamaguchi, Tokyo; Hiroshi Murayama, Houya; Ryohei Kaneko, Kiryu; Katsura Seki, Utsunomiya, all of Japan

[73] Assignee: Taisho Pharmaceutical Co., Ltd., Tokyo, Japan

[21] Appl. No.: 709,180

[22] Filed: Mar. 7, 1985

[30] Foreign Application Priority Data

Sep. 14, 1984 [JP] Japan .................. 59-192787
Sep. 18, 1984 [JP] Japan .................. 59-195469

[51] Int. Cl.$^4$ .......................... A01N 25/00
[52] U.S. Cl. .......................................... 424/84
[58] Field of Search .......................... 424/84

[56] References Cited

U.S. PATENT DOCUMENTS

| | | | |
|---|---|---|---|
| 2,526,859 | 10/1950 | Foreman et al. | 568/322 |
| 2,760,992 | 8/1956 | Schoeffel et al. | 260/505 C |
| 2,831,895 | 4/1958 | Stevens et al. | 568/33 |
| 3,033,903 | 5/1962 | Loeb | 260/351 |

FOREIGN PATENT DOCUMENTS 0064601 4/1982 Japan .................. 424/84

OTHER PUBLICATIONS

Chemical Abstracts [Index] 92: 22617h.
Abstract Japanese Patent Laid Open No. 29502/1981.
Abstract Japanese Patent Laid Open No. 30905/1981.
Abstract Japanese Patent Laid Open No. 30940/1981.
Abstract Japanese Patent Laid Open No. 79602/1981.
Abstract Japanese Patent Laid Open No. 79640/1981.
Abstract Japanese Patent Laid No. 87536/1981.
Abstract Japanese Patent Publication No. 320/1969.
"Abstracts of Papers Presented at the 28th Conference of the Applied Zoological and Entomological Society of Japan", Apr. 2–Apr. 4, 1984, Utsumoniya University, Mine–machi, Utsunomiya City, Japan, by Kimihide Shimano et al, published Mar. 15, 1984, (Japanese text and English translation enclosed).

*Primary Examiner*—Albert T. Meyers
*Assistant Examiner*—John M. Kilcoyne
*Attorney, Agent, or Firm*—Frishauf, Holtz, Goodman & Woodward

[57] ABSTRACT

A method of attracting *Periplaneta americana* L comprising positioning a composition comprising an attractant-ingestion stimulant in a location wherein it is desired to attract *Periplaneta americana* L, said stimulant comprising an amount of at least one compound selected from the group consisting of ar-α-tetralol, ar-β-tetralol, ac-α-tetralol, α-naphthol, β-naphthol and iristectorumin's alcohol effective to attract *Periplaneta americana* L.

14 Claims, No Drawings

ATTRACTANT-INGESTION STIMULANT PREPARATIONS FOR *PERIPLANETA AMERICANA* L

BACKGROUND OF THE INVENTION

1. Field of the Invention

The present invention relates to attractant-ingestion stimulant preparations for *Periplaneta americana* L.

*Periplaneta americana* L is a species of the cockroach which is most known and distributed throughout the world. In Japan, it is the largest species of the house cockroach which is most damage-producing. Among known methods of extermination of the cockroach are ones employing a tackiness plate or toxic bait in which an attractant-ingestion stimulant agent of the invention can be incorporated to enhance the exterminative effects.

2. Description of the Prior Art

As substances which possess attractant effects for the cockroach, there are known sex pheromones produced by extraction from the feces and the mid-gut of *Periplaneta americana* L, several monoterpenoid compounds (see Japanese Patent Laid Open Nos. 29502/1981, 30905/1981, 30940/1981, 79602/1981, 79640/1981, 87536/1981 and others), fatty acids such as myristic acid and palmitic acid, esters thereof and others (see Japanese Patent Publication No. 320/1969).

Extraction of the sex pheromones, however, requires a large number of the insect, *Periplaneta americana* L, and synthesis of the monoterpenoid compounds involves a complicated process. Moreover, the sex pheromones are excitable substances, and the cockroach is hardly immobilized. Also, activities of the sex pheromones are markedly reduced when male and females insects are coexisting [S. TAKAHASHI, C, KITAMURA: Appl. Ent. Zool. 2(3), 133–141 (1972)].

Fatty acids such as myristic acid and palmitic acid and esters thereof not only possess a low attractant activity but also produce no immobilizing or ingestion stimulant effect alone and need addition of starch or sugar.

Accordingly, there have necessarily been increases not only in production cost but also in size of the attractants, with inconvenience in use associated.

SUMMARY OF THE INVENTION

As a result of extensive studies for providing effective cockroach attractants by overcoming the disadvantages of the prior art cockroach attractants, we have found that ar-α-tetralol, ar-β-tetralol, ac-α-tetralol, α-naphthol, β-naphthol and iristectorumin's alcohol, respectively alone, exert a high attractant and ingestion-stimulant activity specific for male *Periplaneta americana* L with decrease in activity when males and females coexist. The present invention has been completed on the basis of the above finding.

This invention is concerned with attractant-ingestion stimulant preparations for *Periplaneta americana* L comprising as the active ingredient one or more members selected from the group consisting of ar-α-tetralol, ar-β-tetralol, ac-α-tetralol, α-naphthol, β-naphthol and iristectorumin's alcohol.

These compounds have chemical names and structures as shown below:

(1) ar-α-Tetralol
   (5,6,7,8-Tetrahydro-1-naphthol)

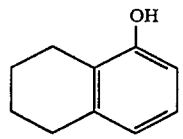

(2) ar-β-Tetralol
   (5,6,7,8-Tetrahydro-2-naphthol)

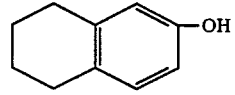

(3) ac-α-Tetralol
   (1,2,3,4-Tetrahydro-1-naphthol)

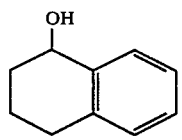

(4) α-Naphthol
   (1-Naphthol)

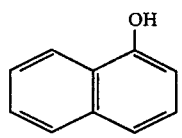

(5) β-Naphthol
   (2-Naphthol)

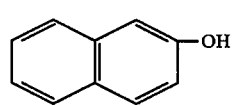

(6) Iristectorumin's alcohol
   (3,7-Dimethyl-10-isopropyl-2,6-cyclodecadien-1-ol)

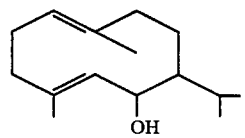

All of the compounds (1)–(5) are, commercially and easily available. Iristectorumin's alcohol is also available by such a method as (a) Photo addition reaction of methylcyclobutene and D-piperitone followed by thermolysis, (b) extraction from *Verbesima iatisquamata* [F. Bohlman: Chem. Ber., 111, 254–263 (1978)], or (c) reduction with LiAlH$_4$ of iristectorumin A obtained from seed oil of *Iristectorum maxim*.

As it is produced in very small quantity by the method (a) or (b), production by the method (c) is desirable.

Various instrumental analyses were carried out to give the following data:

The UV spectrum (EtOH) had an end absorption ($\epsilon$ 6610) at 206 nm;

the IR spectrum (KBr) had characteristic absorptions at 3380, 1660, 1384, 1366 and 845 cm$^{-1}$;

the high resolution mass spectrum had M$^+$ of an m/z of 222 ($C_{15}H_{26}O$); and the PMR (CCl$_4$, 60 MHz) indicated the presence of methyl group at the end of isopropyl group from the absorption 3H, doublet, J=6.6 Hz respectively at 0.95 and 0.97 ppm.

The attractant-ingestion stimulant preparations according to the invention are prepared, for example, in the following manner:

One or more members of the above-mentioned compounds (1)-(6) are dissolved in an appropriate solvent, for example, a hydrophilic organic solvent such as acetone, methanol, ethanol, tetrahydrofuran, ethylene glycol, diethylene glycol or dimethylformamide; and lipophilic organic solvent such as benzene, chloroform, ether, methylene chloride or h-hexane or the like. The resulting solution is impregnated in an appropriate carrier, for example, filter paper, cardboard, nonwoven cloth, cotton cloth or flannel and dried.

Alternatively, attractant tackiness plate, attractant insecticidal sheet or tape or attractant bait can be prepared by incorporating one or more members of the above-mentioned compounds (1)-(6) in a tackiness agent alone or in combination with an insecticide or in bait.

In addition, an attractant-ingestion stimulant preparation in the form of an oil, emulsion, wettable powder, granule, pill, tablet, spray or the like by adding to one or more members of the above-mentioned compounds (1)-(6) an emulsifier, dispersant, penetrant, suspending agent, wetting agent, spreading agent, excipient, stabilizer or the like. Content of the above-mentioned compounds in these preparations is in the range from 0.1 to 20%, preferably from 1 to 5% by weight.

Actions of the attractant-ingestion stimulant preparations of the invention will be described below with reference to Test Examples.

TEST EXAMPLE 1

As test insects were used groups of 100 male and female (1:1) adults one month old after emergence of Periplaneta americana L, Periphaneta fuliginosa S, Periplaneta japonica K, Periplaneta australasiae F, Periplaneta brunnea B, Blatta orientalis L or Blattella germanica L.

Test agents were the above-mentioned compounds (1)-(6).

On the filter paper (Toyo Filter Paper No. 2) 11 cm. in diameter were drawn two circles each 3.5 cm$^2$ in size at an equal distance. To one of the circles was applied a solution containing 1000 μg. of one of the test compounds and to the other 1000 μg. of acetone. The filter paper was air dried to evaporate the solvent thoroughly thereby preparing a test paper.

A group of the test insects was placed individually in a cage which was a transparent polycarbonate vessel 35×30×18 cm. in size. The insects were reared under conditions of 25° C. and 12L-12D (12-hour light period and 12-hour dark period) for orientation in the vessel, in which one of the test papers was then placed. After 24 hours, the test paper was recovered and examined for the degree of ingestion.

The test compounds exerted attractant-ingestion stimulant activities specific for Periplaneta americana L. Results are shown in Table 1.

TABLE 1

| Spot | Periplaneta americana L | Periplaneta fuliginosa S | Periplaneta japonica K | Periplaneta australasiae F | Periplaneta brunnea B | Blatta orientalis L | Blattella germanica L |
|---|---|---|---|---|---|---|---|
| ar-α-Tetralol | 3+, 3+ | —, — | —, — | —, — | —, — | —, — | —, — |
| ar-β-Tetralol | 3+, 3+ | —, — | —, — | —, — | —, — | —, — | —, — |
| ac-α-Tetralol | +, + | —, — | —, — | —, — | —, — | —, — | —, — |
| α-Naphthol | 3+, 3+ | —, — | —, — | —, — | —, — | —, — | —, — |
| β-Naphthol | 2+, 2+ | —, — | —, — | —, — | —, — | —, — | —, — |
| Iristectorumin's alcohol | 3+, 3+ | —, — | —, — | —, — | —, — | —, — | —, — |
| Blank | —, — | —, — | —, — | —, — | —, — | —, — | —, — |

(Note)
3+: Very vigorous marks of biting passing through the filter paper.
2+: Vigorous marks of biting.
+: 4–10 marks of biting.
±: 2–3 marks of biting.
—: No mark of biting.

TEST EXAMPLE 2

As test insects were employed groups of 100 insects of the same sex and instar each consisting of male adults, female adults, male larvae or female larvae of Periplaneta americana L and groups of 100 insects of different sexes and instars consisting of 25 male adults, 25 female adults, 25 male larvae and 25 female larvae (called male and female coexistence group). (The adults were the ones one month after emergence and the larvae were the middle instar ones four months after hatchings).

Test agents were the above-mentioned compounds (1)-(6).

The same test procedures as in Test Example 1 were employed except that the amount of the test compound applied was 200 μg. Degrees of ingestion were examined for the groups of the same sex and instar and the male and female coexistence groups.

The test compounds exerted attractant-ingestion stimulant activities specific for male adults and larvae. There was no reduction in activity observed in the male and female coexistence groups. Results are shown in Table 2.

TABLE 2

| Test agent | Adult Male | Adult Female | Larva Male | Larva Female | Male/female coexistence |
|---|---|---|---|---|---|
| ar-α-Tetralol | 2+, 2+ | ±, — | +, 2+ | —, — | 2+, 2+ |
| ar-β-Tetralol | 2+, 2+ | ±, — | 2+, 2+ | —, — | +, 2+ |
| ac-α-Tetralol | +, + | —, — | +, ± | —, — | +, + |
| α-Naphthol | 2+, 2+ | —, — | 2+, 2+ | —, — | 2+, 2+ |

TABLE 2-continued

| Test agent | Adult Male | Adult Female | Larva Male | Larva Female | Male/female coexistence |
|---|---|---|---|---|---|
| β-Naphthol | 2+, 2+ | ±, ± | 2+, 2+ | —, — | +, 2+ |
| Iristectorumin's alcohol | 3+, 3+ | —, — | 3+, 3+ | —, — | 3+, 3+ |

(Note)
3+, 2+, +, ± and — are the same ratings as defined in Test Example 1.

TEST EXAMPLE 3

As test insects were employed groups of 100 male adults of *Periplaneta americana* L one month old after emergence.

Test compounds were oleic acid, myristic acid, lauryl alcohol, pentadecanol, octyl alcohol, bornyl acetate, nerol, 2-hydroxy-1-naphthoic acid, decaline, naphthalene, tetraline, ar-α-tetralol, ar-β-tetralol, α-naphthol, β-naphthol, ac-α-tetralol, iristectorumin's alcohol and acetone as well as 1:1 mixtures thereof with sucrose.

The same test procedures as in Test Example 1 were employed, and the test papers were recovered after 12-hour dark period to examine the degree of ingestion for each of the test compounds.

ar-α-Tetralol, ar-β-tetralol, α-naphthol, β-naphthol, acα-tetralol and iristectorumin's alcohol exerted attractant-ingestion stimulant activities specific for male adults of *Periplaneta americana* L without the addition of sucrose.

Results are shown in Table 3.

TABLE 3

| Test agent | Alone | 1:1 mixture with sucrose |
|---|---|---|
| Oleic acid | ±, ± | 3+, 3+ |
| Myristic acid | ±, ± | 3+, 3+ |
| Lauryl alcohol | ±, — | 2+, 2+ |
| Pentadecanol | —, — | 2+, 2+ |
| Octyl alcohol | —, — | —, — |
| Bornyl acetate | —, — | —, — |
| Nerol | —, ± | ±, + |
| 2-Hydroxy-1-naphthoic acid | —, — | —, — |
| Decaline | —, — | —, — |
| Naphthalene | —, — | —, ± |
| Tetraline | —, — | —, — |
| ar-α-Tetralol | 3+, 3+ | 3+, 3+ |
| ar-β-Tetralol | 3+, 3+ | 3+, 3+ |
| α-Naphthol | 3+, 3+ | 3+, 3+ |
| β-Naphthol | 2+, 2+ | 2+, 2+ |
| ac-α-Tetralol | +, + | +, + |
| Iristectorumin's alcohol | 3+, 3+ | 3+, 3+ |
| Acetone | —, — | ±, + |

(Note)
3+, 2+, +, ± and — are the same ratings as defined in Test Example 1.

TEST EXAMPLE 4

As test insects were employed male adults one month old after emergence and male middle instar larvae four months old after hatching.

Test agents were the above-mentioned compounds (1)–(6), each of which was impregnated in a round test paper 1 cm. in diameter at various concentrations in the same way as in Test Example 1.

One piece of the round test papers was placed at the bottom of a vinyl chloride cup ca. 8.5 cm. in diameter and ca. 10 cm. in height, into which one test insect was released.

The test paper was recovered after 12-hour dark period and examined for the mark of ingestion. The $BR_{50}$ (μg.) was determined.

Results are shown in Table 4.

TABLE 4

| | $BR_{50}$ (μg.) | |
|---|---|---|
| Test agent | Male adult of *Periplaneta americana* L | Male larva of *Periplaneta americana* L |
| ar-α-Tetralol | 2.0 | 12.3 |
| ar-β-Tetralol | 2.7 | 12.3 |
| α-Naphthol | 12.3 | >50 |
| β-Naphthol | 31.6 | >100 |
| ac-α-Tetralol | >100 | >100 |
| Iristectorumin's alcohol | 4.5 | 21.9 |

TEST EXAMPLE 5

Groups of 100 male adults of *Periplaneta americana* L one month old after emergence were employed as test insects.

Test agents were the above-mentioned compounds (1)–(6) and sucrose, which were treated in the same way as in Test Example 1 except that various concentrations of application were employed for the measurement of activity.

The compounds (1)–(6) had much higher ingestion-stimulant activities than activities of sucrose. Results are shown in Table 5.

TABLE 5

| | Concentration (μg./cm.$^2$) | | | | |
|---|---|---|---|---|---|
| Test agent | 285.7 | 142.9 | 71.4 | 28.6 | 14.3 |
| ar-α-Tetralol | 3+, 3+, 3+ | 3+, 3+, 3+ | 3+, 3+, 3+ | 3+, 3+, 3+ | 2+, 2+, 2+ |
| ar-β-Tetralol | 3+, 3+, 3+ | 3+, 3+, 3+ | 3+, 3+, 3+ | 2+, 2+, + | 2+, +, + |
| ac-α-Tetralol | +, +, + | +, ±, + | ±, ±, ± | ±, —, — | —, —, — |
| α-Naphthol | 3+, 2+, 3+ | 2+, 2+, 3+ | 2+, 2+, 2+ | 2+, +, + | —, ±, ± |
| β-Naphthol | 2+, 2+, + | 2+, +, + | +, +, + | ±, ±, — | —, ±, — |
| Iristectorumin's alcohol | 3+, 3+, 3+ | 3+, 3+, 3+ | 3+, 2+, 2+ | 2+, +, 2+ | 2+, +, + |
| Sucrose | —, ±, — | —, —, — | —, —, — | —, —, — | —, —, — |

(Note)
3+, 2+, +, ±, and — are the same ratings as defined in Test Example 1.

TEST EXAMPLE 6

(1) The test agents were the above-mentioned compounds (1)–(6), which were impregnated respectively in a round filter paper (Toyo Filter Paper No. 2) 1 cm. in diameter in an amount of 1000 μg. in the same way as in Test Example 4 to prepare an attractant preparation.

Attractant baits were also prepared in small granule by kneading 75 parts of fish meal powder, 5 parts of maltose, 5 parts of L-arabinose, 5 parts of oleic acid and 10 parts of rice bran with some water.

(2) 60 male adults of *Periplaneta americana* L one month old after emergence were release in a room approximately 6 mats (ca. 10 m$^2$) in size one week prior to initiation of the test and reared with sufficient bait and water given.

A set of traps, Trap A with the above-mentioned round attractant preparation, Trap B with the above-mentioned granular attractant bait (0.7 g.) and Trap C without the attractant, respectively mounted at the center of the tackiness surface of a cockroach catcher described in Japanese utility Model application Laid-Open No. 142679/1979, was placed in the room, and after 24 hours, examined for number of the cockroach caught.

The experiment was repeated three times, and the average number of the caught cockroach was taken.

Results are shown in Table 6.

TABLE 6

| Test agent | Number of the cockroach caught | | |
|---|---|---|---|
| | Trap A | Trap B | Trap C |
| ar-α-Tetralol | 44 | 16 | 0 |
| ar-β-Tetralol | 41 | 15 | 4 |
| α-Naphthol | 35 | 18 | 5 |
| β-Naphthol | 32 | 21 | 7 |
| ac-α-Tetralol | 23 | 19 | 18 |
| Iristectorumin's alcohol | 36 | 20 | 4 |

TEST EXAMPLE 7

| (1) (Test bait) | |
|---|---|
| ar-α-Tetralol | 1 part |
| Boric acid | 10 parts |
| Soluble starch | 15 parts |
| Potato starch | 15 parts |
| Water | 59 parts |
| | 100 parts |
| (Control bait) | |
| Boric acid | 10 parts |
| Soluble starch | 15 parts |
| Potato starch | 15 parts |
| water | 60 parts |
| | 100 parts |

Granular test bait and control bait of the above-mentioned formulae were prepared by conventional procedures.

(2) In rooms A and B each 6 mats (ca. 10 m$^2$) in size were released 20 male adults one month old after emergence and 20 male larvae four months old after hatching, respectively, which were reared with sufficient bait and water. There were placed the test bait prepared under (1) above in Room A and the control bait in Room B respectively at 5 spots in the same amount. Number of dead cockroach was counted after 5 days.

Results are shown in Table 7.

TABLE 7

| | Number of the dead | Percent extermination (%) |
|---|---|---|
| Test bait | 38 | 95 |
| Control bait | 12 | 30 |

The attractant-ingestion stimulant preparations according to the present invention have attractant-ingestion stimulant activities specific for male cockroach *Periplaneta americana* L and selectively catch the male cockroach only thereby inhibiting fertilization of the female cockroach and producing high effects in extermination of the cockroach.

The attractant-ingestion stimulant agents used in the invention have high attractant-ingestion stimulant activities even when employed alone. As there is no need of adding starch, sugar or the like in preparing the attractant-ingestion stimulant preparations according to the invention, the preparations are advantageous in low cost of production and convenience in use because of smaller sizes of the preparations.

The invention will be described below in embodiment with reference to the examples.

EXAMPLE 1

To ca. 200 ml. of n-hexane was added 1 g. of ar-α-tetralol. The mixture was well stirred by a stirrer for about 10 minutes to give a solution. The solution was impregnated, using an automatic dispenser, uniformly in a nonwoven cloth 20 cm. in width, 50 cm. in length and 0.1 cm. in thickness which was air dried to evaporate the n-hexane.

The impregnated cloth was cut by a cutter to pieces 0.5 cm. in width and 20 cm. in length to prepare attractant-ingestion stimulant tapes.

The tape can be used by mounting at the center of the tackiness plate in a cockroach catching vessel.

Attractant-ingestion stimulant tapes were prepared in the same way as above using ar-β-tatralol, ac-α-tetralol, α-naphthol, β-naphthol or iristectorumin's alcohol.

EXAMPLE 2

A mixture of 10 g. of ar-α-tetralol or iristectorumin's alcohol, 100 g. of boric acid, 150 g. of soluble starch, 150 g. of potato starch and 590 g. of water was molded in an appropriate size to prepare a bait preparation.

EXAMPLE 3

A mixture of 4 g. of α-naphthol or iristectorumin's alcohol, 20 g. of white vaseline and 76 g. of permethrin was applied to a polyethylene tape 5 cm. in width and 200 m. in length.

The tape was cut to a size 5 cm. in width and 20 cm. in length to prepare an insecticidal tape.

EXAMPLE 4

To ca. 200 ml. of acetone were added 1 g. of ar-β-tetralol and 1 g. of β-naphthol. The mixture was thoroughly shaken to a solution. The solution was impregnated using a hole pipette in an amount of ca. 0.1 ml. in a round filter paper (Toyo Filter Paper No. 2) 3 cm. in diameter, which was air dried to evaporate the acetone.

A simple cockroach trap was produced by placing one piece of the impregnated filter paper in a glass cylinder 13 cm. in diameter and 18 cm. in height inside of which had been coated with vaseline of a width of 5 cm.

EXAMPLE 5

A mixture of 10 g. of ar-α-tetralol or iristectorumin's alcohol, 200 g. of natural rubber, 780 g. of a tackifier agent and 10 g. of an antioxidant was thoroughly kneaded and applied using a roll to a cardboard 9 cm. in width and 20 cm. in length which was used as a tackiness plate in the cockroach catching vessel.

What we claim is:

1. A method of attracting *Periplaneta americana* L comprising applying a composition comprising an attractant-ingestion stimulant agent in a location wherein Periplaneta americana L are present in the environment, said attractant-ingestion stimulant agent comprising an amount of at least one compound selected from the group consisting of ar-α-tetralol, ar-β-tetralol, ac-α-tetralol, α-naphthol, β-naphthol and iristectorumin's alcohol effective to attract *Periplaneta americana* L whereby *Periplaneta americana* L are attracted to said composition.

2. The method of claim 1, wherein said composition is applied in a trap for *Periplaneta americana* L.

3. The method of claim 1, wherein said composition includes a component which is toxic to *Periplaneta americana* L thereby becoming a toxic bait.

4. The method of claim 1 wherein said composition comprises said attractant-ingestion stimulant in an amount of from 0.1 to 20% by weight.

5. The method of claim 4 wherein said attractant-ingestion stimulant is ar-α-tetralol.

6. The method of claim 4 wherein said attractant-ingestion stimulant is ar-β-tetralol.

7. The method of claim 4 wherein said attractant-ingestion stimulant is ac-α-tetralol.

8. The method of claim 4 wherein said attractant-ingestion stimulant is α-naphthol or β-naphthol.

9. The method of claim 4 wherein said attractant-ingestion stimulant is iristectorumin's alcohol.

10. The method of claim 5 wherein said composition contains said attractant-ingestion stimulant in an amount of from 1 to 5% by weight.

11. The method of claim 6 wherein said composition contains said attractant-ingestion stimulant in an amount of from 1 to 5% by weight.

12. The method of claim 7 wherein said composition contains said attractant-ingestion stimulant in an amount of from 1 to 5% by weight.

13. The method of claim 8 wherein said composition contains said attractant-ingestion stimulant in an amount of from 1 to 5% by weight.

14. The method of claim 9 wherein said composition contains said attractant-ingestion stimulant in an amount of from 1 to 5% by weight.

* * * * *